(12) United States Patent
Walter et al.

(10) Patent No.: US 7,999,126 B2
(45) Date of Patent: Aug. 16, 2011

(54) PALLADIUM(0)-DIBENZYLIDENE ACETONE COMPLEXES

(75) Inventors: Richard Walter, Alzenau (DE); Horst Meyer, Altenstadt (DE); Steffen Voss, Hanau (DE)

(73) Assignee: W.C. Heraeus GmbH, Hanau (DE)

( * ) Notice: Subject to any disclaimer, the term of this patent is extended or adjusted under 35 U.S.C. 154(b) by 0 days.

(21) Appl. No.: 12/595,628

(22) PCT Filed: Apr. 9, 2008

(86) PCT No.: PCT/EP2008/002785
§ 371 (c)(1),
(2), (4) Date: Oct. 13, 2009

(87) PCT Pub. No.: WO2008/128644
PCT Pub. Date: Oct. 30, 2008

(65) Prior Publication Data
US 2010/0167408 A1 Jul. 1, 2010

(30) Foreign Application Priority Data
Apr. 18, 2007 (DE) .......................... 10 2007 018 703

(51) Int. Cl.
*C07F 15/00* (2006.01)
(52) U.S. Cl. .......................................... 556/136; 436/76
(58) Field of Classification Search ................. 556/136; 436/76
See application file for complete search history.

(56) References Cited

U.S. PATENT DOCUMENTS
4,347,232 A 8/1982 Michaelson

FOREIGN PATENT DOCUMENTS
WO 2004 058784 7/2004

OTHER PUBLICATIONS

Mattison et al., Journal of Polymer Science: Part A, vol. 1, No. 11, pp. 3449-3458 (1963).*
Rettig et al; "Tetrakis(tert-Butylisocyanided)di-μ-chloro-dipalladium(I)"; Innorganic Synthesis, vol. 28, 1990, pp. 110-113[cited in application, p. 111, paragraph 1].
Ukai, et al, "Chemistry of dibenzylideneacetone-palladium(0) complexes"; Journal of Organometallic Chemistry, vol. 65, (1974), pp. 253-266 [cited in application].

* cited by examiner

*Primary Examiner* — Porfirio Nazario Gonzalez
(74) *Attorney, Agent, or Firm* — Norris McLaughlin & Marcus, P.A.

(57) ABSTRACT

Palladium(0)-dibenzylidene acetone complexes $Pd_x(dba)_y$, with y/x being from 1.5 to 3, are provided according to the invention at a purity of at least 99.5 wt. %. The use of said $Pd_x(dba)_y$ complexes according to the invention is for determining their stoichiometry by means of elemental analysis. In the method for the production of $Pd_x(dba)_y$ complexes from a Pd-containing educt and dibenzylidene acetone (dba) in alcohol, according to the invention a solution of the dba in alcohol pre-heated to more than 40° C. is provided first and then the Pd-containing educt is added to the pre-heated solution upon which the complexes are precipitated by a base.

12 Claims, No Drawings

PALLADIUM(0)-DIBENZYLIDENE ACETONE COMPLEXES

This application is a 371 of PCT/EP2008/002785, filed 9 Apr. 2008, which claims foreign priority benefit under 35 U.S.C. §119 of the German Patent Application No. 10 2007 018 703.5, filed 18 Apr. 2007.

The invention relates to palladium(0)-dibenzylidene acetone complexes $Pd_x(dba)_y$ and methods for the production thereof. Complexes of this type are used for C—C coupling reactions.

Y. Takahashi et al., Journal of the Chemical Society, Chemical Communications 1065 (1970) and Inorganic Synthesis, 28, 110 (1990), describes a palladium(0) complex $Pd(dba)_2$. It is produced by adding sodium acetate (NaAc) and an excess of dba (dba: Pd>=3) to a hot methanolic $Na_2PdCl_4$ (Takahashi) or $PdCl_2$ solution (Inorganic Synthesis). The solution is allowed to cool while stirring upon which the complex precipitates. The complex is then collected by filtration and washed first with water and then with acetone.

T. Ukai et al., J. Organomet. Chem. 65, 253 (1974), discloses the synthesis of palladium(0) dibenzylidene acetone complexes as $Pd_2(dba)_3 \times CHCl_3$. For this purpose, $PdCl_2$ is added to a hot solution of dba-NaOAc and methanol. The mixture is stirred for 4 hours at 40° C. upon which the product precipitates and is recrystallised in chloroform. The chloroform remains bound to the complexes.

Herrmann/Brauer, Synthetic Methods of Organometallic and Inorganic Chemistry, vol. 1, 160 (1996) describes the synthesis of $Pd_2(dba)_3 \times dba$ and refers to T. Ukai and Y. Takahashi as mentioned above. Products that have been reproduced accordingly are contaminated by substantial insoluble fractions.

M. C. Mazza, C. G. Pierpont, Inorg. Chem., 12, 2955 (1973) describes the synthesis of $Pd(dba)_3 \times C_6H_6$.

M. C. Mazza, C. G. Pierpont, J. C. S., Chem. Comm., 207 (1973) describes the synthesis of $Pd_2(dba)_3 \times CH_2Cl_2$.

The products described in the literature have not been fully characterised. Accordingly, neither the palladium content of the compounds nor the composition are described exactly in the preceding literature reference. The underlying reason is presumably the inability to purify the product for lack of a suitable solvent. Upon dissolution in CHC or aromatic hydrocarbons, new products are generated by reaction with the solvent.

M. C. Mazza and C. G. Pierpont (Inorg. Chem., 12, 2955 (1973)) conclude that there exists a reversible series of Pd-dba complexes: $Pd_2(dba)_3$, $Pd(dba)_2$, and $Pd(dba)_3$ with Pd contents of 23.2%, 18.5%, and 13.1%, respectively.

According to P. Espinet, A. M. Echavarren (Angew. Chem. 2004, 116, 4808), the term, as a dimetal complex, $[Pd_2(dba)_3]*dba$, is more exact than $Pd(dba)_2$.

The analysis of $Pd_x(dba)_y$ complexes is difficult since the insoluble ingredients falsify the result of elemental analysis and dissolution of the $Pd_x(dba)_y$ complexes instantaneously leads to other compounds, in which the solvent is addition-complexed.

In the large-scale production of the palladium(0)-dibenzylidene acetone complexes, it is essential to obtain a crystalline product at high yield that has high purity and can be easily subjected to filtration. For cost-efficient production of the compound it is also crucial to keep the drying times as short as possible. Regarding the purity, it is absolutely crucial that the compound contains no or only small quantities of insoluble fractions when it is dissolved, e.g., in CHC or aromatic hydrocarbons. This ensures that all of the Pd present in the product is available for the catalytic application of the product. Insoluble Pd-containing fractions and, in particular, metallic Pd are not available in homogeneous catalytic processes. Contaminants of this type are therefore undesirable.

It is the object of the invention to increase the purity of palladium(0)-dibenzylidene acetone complexes, to minimize the insoluble fractions for this purpose, and, in particular, to prevent the addition-complexation of chlorinated hydrocarbons.

In order to meet this object, $Pd(dba)_2$ having smaller insoluble fractions is provided by reacting a Pd-containing educt, in particular Pd salt, with dibenzylidene acetone and sodium acetate in alcohol. For this purpose, dibenzylidene acetone in alcohol is provided, in particular dissolved, and heated to 57° C. The Pd-containing educt, in particular Pd salt, e.g. $PdCl_2$, $H_2PdCl_4$, $(NH_4)_2PdCl_4$, $Na_2PdCl_4$ or $K_2PdCl_4$, is then dissolved in the heated solution and sodium acetate is added. $Pd(dba)_2$ precipitates from the solution which is cooled in order to promote complete separation. The precipitated product is subjected to filtration, washed first with alcohol and then with petroleum spirit, and dried in vacuo at 40° C. Very pure $Pd(dba)_2$ can be produced by this means. Halogen-containing, in particular chlorinated, hydrocarbons were avoided in the production of the complexes. The molar ratio of palladium to dibenzylidene acetone of the product obtained is in the range of 1:2±0.1. By this means, the purity of palladium(0)-dibenzylidene acetone complexes, relative to CHC-insoluble fractions, that can be provided is 99, preferably 99.5, in particular 99.9 wt. %, with the predominant fraction presumably being $Pd(dba)_2$. Accordingly, the insoluble fractions are reduced to less than 1 wt. %, in particular 1 wt. %. Halogen-containing, in particular chlorine-containing, compounds are basically absent. Moreover, aromatic solvents are not included in the complexes. According to the invention, neither halogen-containing nor aromatic solvents are used. Using pure starting products, contamination by CHC or aromatic hydrocarbons are easy to keep at less than 1 wt. %, in particular at less than 100 ppm and preferably at less than 10 ppm.

According to the invention, palladium(0)-dibenzylidene acetone complexes with a palladium content of 19 to 23 wt. %, in particular 20 to 21 wt. %, are provided by providing dibenzylidene acetone in alcohol in the reactor and heating to 60° C. A Pd-containing educt, in particular Pd salt, e.g. $H_2PdCl_4$, $(NH_4)_2PdCl_4$, $K_2PdCl_4$, $Na_2PdCl_4$, or $PdCl_2$, is then dissolved in this. Sodium acetate is added, and cooled, in order to precipitate the product of the reaction. The precipitated product is subjected to filtration, washed first with alcohol and then with petroleum spirit, and dried in vacuo at 40° C. The CHC-insoluble contaminants account for less than 1 wt. %. The high palladium content is accompanied by a high fraction of $Pd_2(dba)_3$.

According to the invention, palladium(0)-dibenzylidene acetone complexes with a palladium content of 13 to 17 wt. %, in particular 15 to 16.5 wt. % are provided, by heating dibenzylidene acetone in alcohol to 50° C. before adding the Pd-containing educt, in particular as chloride, e.g. $PdCl_2$, $H_2PdCl_4$, $(NH_4)_2PdCl_4$, $Na_2PdCl_4$ or $K_2PdCl_4$. Sodium acetate is added and the reaction mixture is cooled in order to precipitate the product of the reaction, the precipitated product is subjected to filtration, washed first with alcohol and then with petroleum spirit, and, lastly, dried in vacuo at 40° C. The contaminants account for less than 1 wt. %. The low palladium content is accompanied by a high fraction of $Pd(dba)_3$.

According to the invention, $Pd_x(dba)_y$ complexes who are contaminated by less than 5%, preferably less than 1%, of organic solvents or CHC-insoluble Pd fractions are provided.

The remaining traces of contaminants are essentially alcohol and petroleum spirit. The $Pd_x(dba)_y$ complexes $Pd(dba)_3$, $Pd(dba)_2$, and $Pd_2(dba)_3$ have been produced. The stoichiometry of the $Pd_x(dba)_y$ complexes is therefore between $Pd(dba)_3$ and $Pd_2(dba)_3$.

COMPARATIVE EXAMPLES

1.) Synthesis According to Inorganic Synthesis, 28, 110 (1990)

The synthesis is carried out under inert gas. 2.096 g (11.73 mmol) $PdCl_2$ and 0.686 g (11.73 mmol) NaCl are provided under argon, and 59 ml of methanol are added.

Next the reaction mixtures is stirred over night for 18 hours in the sealed flask. Then the dark red-brown solution is filtered through a G3 frit under argon. No residue is evident on the frit.

The filtrate solution is transferred to a 500 ml three-necked flask using 293 ml of methanol, and heated to 60° C. At this temperature, 8.563 g (36.54 mmol) dibenzylidene acetone are added under argon. Then, the addition of 17.595 g (214.49 mmol) sodium acetate is made.

A voluminous, reddish solid precipitates. Subsequently, the reaction mixture is cooled to room temperature. The product is removed by filtration and washed with 300 ml of methanol, 300 ml of water, and 300 ml of acetone. The product is dried in vacuo at room temperature.

Appearance: dark-brown solid
Solubility Test:

1.00 g of the product are dissolved in 150 ml of chloroform and stirred at room temperature for 30 minutes. The solution is then aspirated through a membrane filter. The filter is washed with 30 ml of water and 30 ml of acetone and subsequently dried over night at 45° C. in vacuo. The residue accounts for 1.4%.

Result:
m(product): 6.4 g
Yield with respect to Pd: 94
$CHCl_3$-insoluble ingredients: 1.4
Analysis:

|  | Pd [%] | C [%] | O [%] | H [%] |
|---|---|---|---|---|
| Theoretical | 18.5 | 71.0 | 5.6 | 4.9 |
| Actual | 18.2 | 71.08 | 5.65 | 4.92 |

2.) Synthesis According to Y. Takahashi et al

J. Chem. Soc. Chem. Commun. 1065 (1970)

The synthesis is carried out under inert gas.

1.55 kg (6616 mmol) dibenzylidene acetone, 657.9 g (2208 mmol) $Na_2PdCl_4$, and 56 l methanol are heated to 57° C. in the reaction flask. Then, the addition of 1.47 kg (17920 mmol) sodium acetate is made. A voluminous, reddish solid precipitates.

Subsequently, the reaction mixture is allowed to cool to room temperature. The product is removed by filtration and washed with 50 l of water and 50 l of acetone. The product is dried in vacuo at room temperature.

Appearance: dark-brown solid
Solubility Test:

1.00 g of the product were dissolved in 150 ml of chloroform and stirred for 30 minutes at room temperature. The solution was aspirated through a membrane filter. The filter was washed with 30 ml of water and 30 ml of acetone and subsequently dried over night at 45° C. in vacuo. The residue accounts for 1.1%.

Result:
m(product): 1053 g
Yield with respect to Pd: 93
$CHCl_3$-insoluble ingredients: 1.1 wt. %
Analysis:

|  | Pd [%] | C [%] | O [%] | H [%] |
|---|---|---|---|---|
| Theoretical | 18.5 | 71.0 | 5.6 | 4.9 |
| Actual | 20.8 | 68.08 | 5.93 | 4.92 |

Experiment 1

The synthesis was carried out under inert gas. 300 ml of methanol were provided in the reaction flask under argon and heated to 57° C. Then 8.245 g (35.2 mmol) dibenzylidene acetone and 3.495 g (1.248 g Pd, 11.7 mmol Pd) $Na_2[PdCl_4]$ were added in the presence of an argon flow.

Then, 7.80 g (95.1 mmol) anhydrous Na-acetate were added to the reaction mixture at 57° C. After cooling to room temperature, the stirrer was switched off and the mixture allowed to stand for 1.5 h upon which the product sedimented. The supernatant mother liquor was decanted and the product was washed with 300 ml of washing solution (methanol/fully demineralised water=1/1) to be free of NaCl. The product was washed with 70 ml of water (chloride test: negative) and subsequently with 300 ml of acetone and 200 ml of petroleum spirit. The product was dried over night in vacuo at 40° C.

Appearance: reddish-brown solid
Solubility Test:

1.00 g of the product were dissolved in 150 ml of chloroform and stirred for 30 minutes at room temperature. The solution was aspirated through a membrane filter. The filter was washed with 30 ml of water and 30 ml of acetone, and the filter was subsequently dried over night at 45° C. in vacuo. The residue accounted for 0%.

Result:
m(product): 6.4 g
Yield with respect to Pd: 95.4%
$CHCl_3$-insoluble ingredients: 0%
Analysis:

|  | Pd [%] | C [%] | O [%] | H [%] |
|---|---|---|---|---|
| Theoretical $Pd(dba)_2$ | 18.5 | 71 | 5.6 | 4.9 |
| Actual | 18.6 | 70.81 | 5.66 | 4.85 |

Experiment 2

The synthesis was carried out as in Experiment 1, except for the reaction being carried out at a starting temperature of 50° C.

Result:
m(product): 7.05 g
Yield with respect to Pd: 92.4
$CHCl_3$-insoluble ingredients: 0.2

Analysis:

|  | Pd [%] | C [%] | O [%] | H [%] |
|---|---|---|---|---|
| Theoretical Pd(dba)$_2$ | 18.5 | 71 | 5.6 | 4.9 |
| Actual | 16.35 | 72.47 | 5.75 | 5.02 |

Experiment 3

The synthesis was carried out as in Experiment 1, except for the sample being four times larger. The reaction was carried out at a starting temperature of 60° C.
Result:
m(product): 24.682 g
Yield with respect to Pd: 96.4%
CHCl$_3$-insoluble ingredients: 0.2%
Analysis:

|  | Pd [%] | C [%] | O [%] | H [%] |
|---|---|---|---|---|
| Theoretical Pd(dba)$_2$ | 18.5 | 71 | 5.6 | 4.9 |
| Actual | 19.5 | 70.34 | 5.41 | 4.8 |

Experiment 4

The synthesis was carried out as in Experiment 3. The reaction was carried out at a starting temperature of 60° C.
Result:
m(product): 25.0 g
Yield with respect to Pd: 96.2%
CHCl$_3$-insoluble ingredients: 0%
Analysis:

|  | Pd [%] | C [%] | O [%] | H [%] |
|---|---|---|---|---|
| Theoretical Pd(dba)$_2$ | 18.5 | 71 | 5.6 | 4.9 |
| Actual | 19.2 | 70.55 | 5.59 | 4.96 |

Experiment 5

The synthesis was carried out as in Experiment 1, except for the reaction being carried out at a starting temperature of 60° C. and being maintained at this temperature for 5 minutes; the cooling commenced only thereafter.
Result:
m(product): 6.15 g
Yield with respect to Pd: 99.5%
CHCl$_3$-insoluble ingredients: 0.1%
Analysis:

|  | Pd [%] | C [%] | O [%] | H [%] |
|---|---|---|---|---|
| Theoretical | 18.5 | 71 | 5.6 | 4.9 |
| Actual | 20.2 | 69.33 | 5.6 | 4.9 |

The invention claimed is:

1. A palladium(0)-dibenzylidene acetone complex Pdx(dba)y, wherein y/x ranges from 1.5 to 3, said complex having a purity of at least 99.5 wt. % with respect to chlorohydrocarbon-insoluble fractions.

2. Palladium(0)-dibenzylidene acetone complex according to claim 1, which has a purity of at least 99.9 wt. % with respect to chlorohydrocarbon-insoluble fractions.

3. Palladium(0)-dibenzylidene acetone complex according to claim 1, which contains less than 1 wt. % halogenated hydrocarbons.

4. Palladium(0)-dibenzylidene acetone complex according to claim 3, which contains less than 100 ppm halogenated hydrocarbons.

5. Palladium(0)-dibenzylidene acetone complex according to claim 4, which contains less than 10 ppm halogenated hydrocarbons.

6. Palladium(0)-dibenzylidene acetone complex according to claim 1, which has a molar ratio of palladium to dibenzylidene acetone in the range of 1:1.5 to 1:1.8.

7. Palladium(0)-dibenzylidene acetone complex according to claim 1, which has a molar ratio of palladium to dibenzylidene acetone in the range of 1:1.8 to 1:2.2.

8. Palladium(0)-dibenzylidene acetone complex according to claim 7, which has a molar ratio of palladium to dibenzylidene acetone in the range of 1:1.9 to 1:2.1.

9. Palladium(0)-dibenzylidene acetone complex according to claim 1, which has a molar ratio of palladium to dibenzylidene acetone in the range of 1:2.5 to 1:3.

10. A method comprising determining the stoichiometry of a Pdx(dba)y complex by means of elemental analysis, wherein the Pdx(dba)y complex is a Pdx(dba)y complex according to claim 1.

11. Method for the production of a Pdx(dba)y complex from a Pd-containing educt and dibenzylidene acetone (dba) in alcohol, comprising first providing a solution of the dba in alcohol pre-heated to more than 40° C. and then adding the Pd-containing educt to the pre-heated solution upon which the complex is precipitated by a base.

12. Palladium(0)-dibenzylidene acetone complex Pdx(dba)y, wherein y/x ranges from 1.5 to 3, said complex having a purity of at least 99.5 wt. % with respect to chlorohydrocarbon-insoluble fractions, and said complex containing less than 1 wt. % halogenated hydrocarbons.

* * * * *

UNITED STATES PATENT AND TRADEMARK OFFICE
CERTIFICATE OF CORRECTION

PATENT NO. : 7,999,126 B2  
APPLICATION NO. : 12/595628  
DATED : August 16, 2011  
INVENTOR(S) : Walter et al.

Page 1 of 1

It is certified that error appears in the above-identified patent and that said Letters Patent is hereby corrected as shown below:

In the Specification

Column 2, line 31, "1 wt. %" -- should read --1 wt. ‰ --.

Column 2, line 37, "1 wt. %" -- should read -- 1 wt. ‰ --.

Column 2, line 66, "5%" -- should read -- 5‰ --.

Column 2, line 66, "1%" -- should read -- 1‰ --.

Column 3, line 40, "94" -- should read -- 94% --.

Column 3, line 41, "1.4" -- should read -- 1.4% --.

Column 4, line 10, "93" -- should read -- 93% --.

Signed and Sealed this  
Twenty-fourth Day of December, 2013

Margaret A. Focarino  
*Commissioner for Patents of the United States Patent and Trademark Office*